US00PP18069P2

(12) United States Plant Patent
Klemm

(10) Patent No.: US PP18,069 P2
(45) Date of Patent: Sep. 25, 2007

(54) ***DIASCIA* PLANT NAMED 'KLEDI04018'**

(50) Latin Name: *Diascia hybrida*
Varietal Denomination: KLEDI04018

(75) Inventor: Nils Klemm, Stuttgart (DE)

(73) Assignee: Klemm + Sohn GmbH + Co. KG, Stuttgart (DE)

( * ) Notice: Subject to any disclaimer, the term of this patent is extended or adjusted under 35 U.S.C. 154(b) by 0 days.

(21) Appl. No.: 11/343,862

(22) Filed: Jan. 31, 2006

(51) Int. Cl.
*A01H 5/00* (2006.01)

(52) U.S. Cl. ..... Plt./263

(58) Field of Classification Search ..... Plt./263
See application file for complete search history.

*Primary Examiner*—Kent Bell
*Assistant Examiner*—June Hwu
(74) *Attorney, Agent, or Firm*—C. A. Whealy

(57) ABSTRACT

A new and distinct cultivar of *Diascia* plant named 'KLEDI04018', characterized by its compact, upright and somewhat outwardly spreading plant habit; freely branching habit; freely flowering habit; light red-colored flowers; and good garden performance.

1 Drawing Sheet

Botanical designation: *Diascia hybrida.*
Cultivar denomination: 'KLEDI04018'.

CROSS-REFERENCE TO RELATED APPLICATIONS

Title: *Diascia* plant named 'KLEDI04015'.

Applicant: Nils Klemm.

Title: *Diascia* plant named 'KLEDI04016'.

Applicant: Nils Klemm.

Title: *Diascia* plant named 'KLEDI04017'.

Applicant: Nils Klemm.

BACKGROUND OF THE INVENTION

The present Invention relates to a new and distinct cultivar of *Diascia* plant, botanically known as *Diascia hybrida,* and hereinafter referred to by the cultivar name 'KLEDI04018'.

The new *Diascia* is a product of a planned breeding program conducted by the Inventor in Stuttgart, Germany. The objective of the breeding program is to create new upright and freely branching *Diascias* with numerous attractive flowers, and good garden performance.

The new *Diascia* originated from a cross-pollination made by the Inventor in 2003 of an unnamed proprietary seedling of *Diascia hybrida,* not patented, as the female, or seed parent, with a proprietary seedling of *Diascia hybrida* identified as code number SG 3, not patented, as the male, or pollen parent. The new *Diascia* was selected as a single plant from the resulting progeny of the cross-pollination by the Inventor in November, 2003, in an controlled environment in Stuttgart, Germany.

Asexual reproduction of the new cultivar by terminal cuttings in a controlled environment in Stuttgart, Germany since November, 2003, has shown that the unique features of this new *Diascia* are stable and reproduced true to type in successive generations.

SUMMARY OF THE INVENTION

Plants of the cultivar 'KLEDI04018' have not been observed under all possible environmental conditions. The phenotype may vary somewhat with variations in environment such as temperature and light intensity without, however, any variance in genotype.

The following traits have been repeatedly observed and are determined to be the unique characteristics of 'KLEDI04018'. These characteristics in combination distinguish 'KLEDI04018' as a new and distinct cultivar of *Diascia:*

1. Compact, upright and somewhat outwardly spreading plant habit.
2. Freely branching habit.
3. Freely flowering habit.
4. Light red-colored flowers.
5. Good garden performance.

Plants of the new *Diascia* differ from plants of the parent selections primarily in plant form as plants of the new *Diascia* are more uniform than plants of the parent selections.

Plants of the new *Diascia* differ primarily from plants of the cultivar 'KLEDI04015', disclosed in a U.S. Plant patent application Ser. No. 11/343,879 filed concurrently; the cultivar 'KLEDI04016', disclosed in a U.S. Plant patent application Ser. No. 11/343,872 filed concurrently; and the cultivar 'KLEDI04017', disclosed in a U.S. Plant patent application Ser. No. 11/343,873 filed concurrently, primarily in flower color.

Plants of the new *Diascia* can be compared to plants of the cultivar Kiedione, disclosed in U.S. Plant Pat. No. 15,564. In side-by-side comparisons, plants of the new *Diascia* differ from plants of the cultivar Kiedione primarily in plant habit as plants of the cultivar Kiedione are more trailing. In addition, plants of the new *Diascia* and the cultivar Kiedione differ in flower color as plants of the cultivar Kiedione have light pink-colored flowers.

BRIEF DESCRIPTION OF THE PHOTOGRAPH

The accompanying colored photograph illustrates the overall appearance of the new cultivar, showing the colors as true as it is reasonably possible to obtain in colored reproductions of this type. Colors in the photograph may differ slightly from the color values cited in the detailed botanical description which accurately describe the colors of the new *Diascia.* The photograph comprises a side perspective view of a typical flowering plant of 'KLEDI04018' grown in a container.

DETAILED BOTANICAL DESCRIPTION

The aforementioned photograph and following observations and measurements describe plants grown in Stuttgart, Germany, in an outdoor nursery during the summer with day temperatures ranging from 20° C. to 35° C., night temperatures ranging from 10° C. to 20° C., and light levels about 20,000 lux. Plants were grown for about 6.5 months in containers and pinched two times. Color references are made to The Royal Horticultural Society Colour Chart, 1995 Edition, except where general terms of ordinary dictionary significance are used.

Botanical classification: *Diascia hybrida* cultivar 'KLEDI04018'.

Parentage:

*Female parent.*—Unnamed proprietary seedling of *Diascia hybrida,* not patented.

*Male parent.*—Proprietary seedling of *Diascia hybrida* identified as code number SG 3, not patented.

Propagation:

*Type cutting.*—Terminal vegetative cuttings.

*Time to initiate roots, summer.*—About 7 days at 25° C.

*Time to initiate roots, summer.*—About 10 days at 25° C.

*Time to produce a rooted young plant, summer.*—About 14 days at 25° C.

*Time to produce a rooted young plant, winter.*—About 17 days at 25° C.

*Root description.*—Fine, fibrous.

*Rooting habit.*—Freely branching.

Plant description:

*Form.*—Compact, upright and somewhat outwardly spreading to eventually semi-trailing plant habit. Freely branching with about 50 lateral branches forming per plant. Moderately vigorous growth habit.

*Plant height.*—About 25 cm to 30 cm.

*Plant diameter.*—About 50 cm to 60 cm.

*Lateral branches* (*peduncles*).—Length: About 25 cm to 40 cm. Diameter: About 2.5 mm. Internode length: About 2 cm to 3.5 cm. Texture: Smooth, glabrous. Color: 137A.

*Foliage description.*—Arrangement: Opposite, simple; sessile. Length: About 1.5 cm to 2.5 cm. Width: About 1 cm to 1.5 cm. Shape: Ovate. Apex: Obtuse. Base: Truncate. Margin: Serrate. Texture, upper and lower surfaces: Smooth, glabrous; leathery. Venation pattern: Pinnate. Color: Developing and fully expanded foliage, upper surface: 147A; venation, 147A. Developing and fully expanded foliage, lower surface: 147B; venation, 147A.

Flower description:

*Flower type and habit.*—Solitary zygomorphic flowers arranged on terminal racemes. Five modified petals fused at base. Flowers not persistent. Flowers face upright, outwardly to drooping.

*Quantity.*—Freely flowering; typically about 35 to 40 flower buds and flowers per lateral branch.

*Natural flowering season.*—Plants flower continuously from spring through the summer in Germany.

*Time to flower.*—Plants begin flowering about ten weeks after planting.

*Flower longevity on the plant.*—About five days.

*Fragrance.*—None detected.

*Inflorescence size.*—Length: About 10 cm. Width: About 4 cm.

*Flower size.*—Diameter: About 1.5 cm to 2 cm. Depth: About 2 cm.

*Flower buds.*—Length: About 1 mm to 2 mm. Diameter: About 2 mm to 3 mm. Shape: Rounded ovoid. Color: Close to 144A.

*Petals.*—Quantity/arrangement: Five modified petals fused at base. Length: About 5 mm to 10 mm. Width: About 1 cm to 1.5 cm. Shape: Ovate. Apex: Obtuse. Margin: Entire. Texture, upper and lower surfaces: Smooth, glabrous; velvety. Color: When opening and fully opened, upper surface: 58B; towards the base, 61A. When opening and fully opened, lower surface: 58C; towards the base, 61A.

*Spur.*—Length: About 4 mm. Width: About 1 mm. Color, upper and lower surfaces: 45D.

*Sepals.*—Arrangement/appearance: Single whorl of five sepals fused at base; star-shaped. Length: About 2 mm. Width: About 1 mm. Shape: Oblong. Apex: Acute. Margin: Entire. Texture, upper and lower surfaces: Smooth, glabrous. Color, upper and lower surfaces: Close to 144A.

*Pedicels.*—Length: About 5 mm to 10 mm. Width: About 1 mm. Angle: Mostly erect, bending with the weight of the flowers. Strength: Weak. Texture: Smooth, glabrous. Color: Close to 144A.

*Reproductive organs.*—Stamens: Quantity per flower: About four. Anther shape: Reniform. Anther length: About 1 mm. Anther color: Close to 9A. Pollen amount: Moderate. Pollen color: Close to 9A. Pistils: Quantity per flower: One. Pistil length: About 2 mm to 3 mm. Style length: About 1 mm. Stigma shape: Pointed. Stigma color: Light green. Seeds: Length: About 0.5 mm to 1 mm. Diameter: About 0.5 mm to 1 mm. Color: Brown.

Disease/pest resistance: Plants of the new *Diascia* have not been noted to be resistant to pathogens or pests common to *Diascia.*

Temperature tolerance: Plants of the new *Diascia* have been observed to tolerate temperatures from about 0° C. to about 35° C. and have good garden performance.

It is claimed:

1. A new and distinct cultivar of *Diascia* plant named 'KLEDI04018', as illustrated and described.

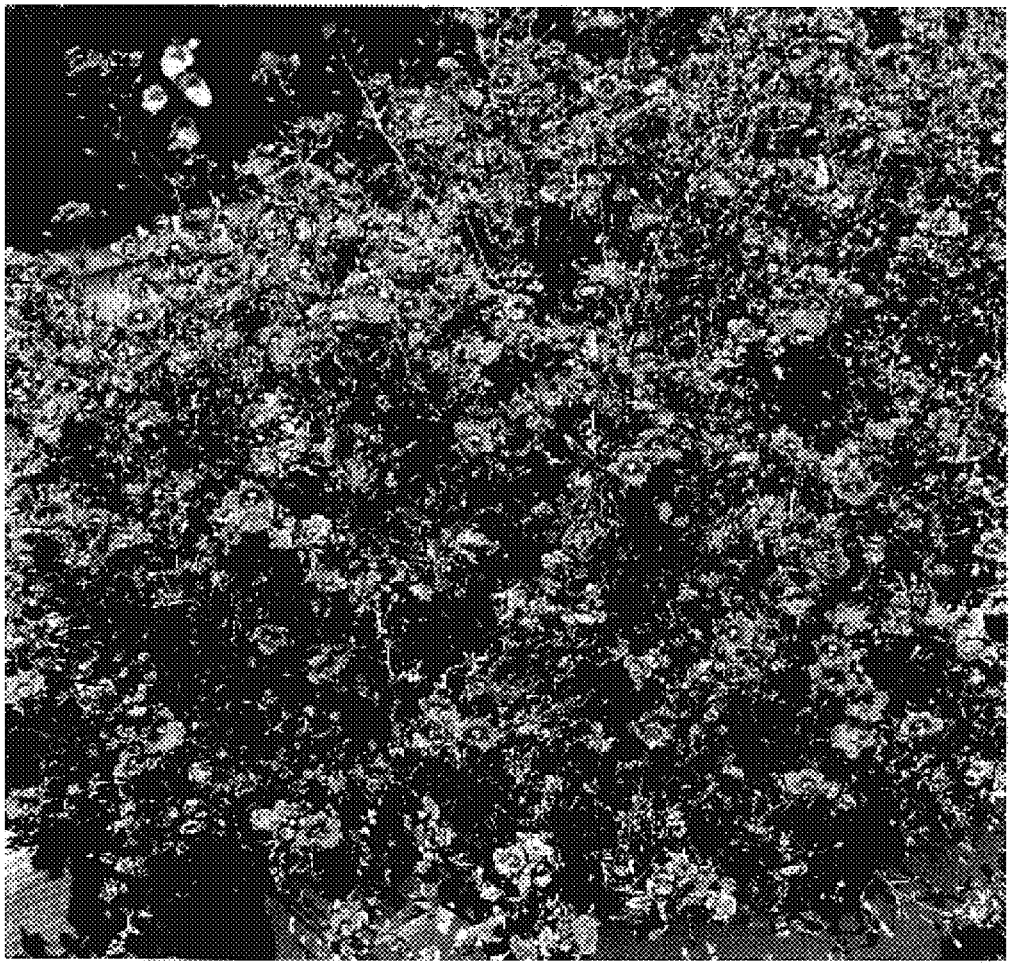

* * * * *